United States Patent [19]

Iovanni et al.

[11] Patent Number: 4,765,975
[45] Date of Patent: Aug. 23, 1988

[54] HAIR CONDITIONING

[75] Inventors: Carl F. Iovanni, Somerville; Duane M. Biesel, Framingham, both of Mass.

[73] Assignee: The Gillette Company, Boston, Mass.

[21] Appl. No.: 836,051

[22] Filed: Mar. 4, 1986

[51] Int. Cl.$^4$ .......................... A61K 7/06; A61K 9/10
[52] U.S. Cl. .......................................... 424/70; 132/7; 514/864
[58] Field of Search ................... 528/401, 402; 424/70

[56] References Cited

U.S. PATENT DOCUMENTS

| | | | |
|---|---|---|---|
| 3,004,961 | 10/1961 | Hauptshein | 528/402 |
| 3,388,078 | 6/1968 | Evans et al. | 528/402 |
| 3,720,630 | 3/1973 | Pittman et al. | 528/402 |
| 3,959,462 | 5/1976 | Parks | 424/70 |
| 3,993,744 | 11/1976 | Cella | 424/70 |
| 3,993,745 | 11/1976 | Cella | 424/70 |
| 4,013,786 | 3/1977 | Cella | 424/70 |
| 4,176,176 | 11/1979 | Cella | 424/70 |
| 4,183,367 | 1/1980 | Goebel | 424/70 |
| 4,187,389 | 2/1980 | Eckhardt | 424/70 |
| 4,374,825 | 2/1983 | Bolich | 424/70 |
| 4,465,802 | 8/1984 | Dennen et al. | 424/70 |
| 4,551,330 | 11/1985 | Wagman | 424/70 |
| 4,563,493 | 1/1986 | Fukui et al. | 528/402 |

FOREIGN PATENT DOCUMENTS

| | | | |
|---|---|---|---|
| 935379 | 10/1973 | Canada | 424/70 |
| 1268636 | 3/1972 | United Kingdom | 424/70 |
| 1598567 | 9/1981 | United Kingdom | 424/70 |
| 2102288 | 2/1983 | United Kingdom | 424/70 |

Primary Examiner—Dale R. Ore

[57] ABSTRACT

An improved hair conditioning composition comprises water, a cationic hair conditioning agent, a nonionic surfactant, a fatty alcohol, and an extremely small but effective amount of a fluorosurfactant, the hair conditioning composition preferably comprising from about 0.5 to 5 percent of the cationic hair conditioning agentm, up to about 5 percent of the nonionic surfactant, from about 0.5 to 10 percent of one or more fatty alcohols, less than 0.05 percent of the fluorosurfactant, and water.

25 Claims, No Drawings

HAIR CONDITIONING

This invention relates to hair conditioning compositions.

Healthy, undamaged hair can be naturally difficult to comb, especially when wet. Damaged hair, such as can result from exposure to excessive heat and dryness (e.g. blowdrying, sun, and wind) and from chemical treatments (e.g. bleaching or coloring and permanents which curl or straighten the hair) can be even more difficult to comb.

Hair conditioning compositions designed to improve the combability of the hair typically contain ionic compounds (e.g. cationic surfactants, designed to reduce static as well as generally condition), oils, waxes, or resins to smooth and coat the hair and impart a sheen to the hair, proteins, humectants, and various perfumes, thickeners, and preservatives. These ingredients are typically combined with a hydrophilic emulsifier to produce an oil-in-water emulsion or with a suspending agent or a thickener (e.g. a cellulose gum). In these formulations, the lipophilic part of the cationic surfactant (the active ingredient) is in the oil phase which, by action of the emulsifier or dispersion agent, exists as small droplets within the larger amount of water (the external phase).

According to one aspect of the invention, an improved hair conditioning composition comprises water, a cationic hair conditioning agent, a nonionic surfactant, a fatty alcohol, and an extremely small but effective amount of a fluorosurfactant, the hair conditioning composition preferably comprising from about 0.5 to 5 percent of the cationic hair conditioning agent, up to about 5 percent of the nonionic surfactant, from about 0.5 to 10 percent of one or more fatty alcohols, less than 0.05 percent of the fluorosurfactant, and water.

It was unexpected that the conditioning compositions of this invention with the extremely small amounts of fluorosurfactant would provide the improved overall combing and other improved conditioning effects. While comparative combing tests indicated a preference for hair conditioning compositions in accordance with the invention with a fluorosurfactant content of about 0.0005 weight percent and a fatty alcohol content of about three weight percent, other hair conditioning compositions in accordance with the invention with similar fatty alcohol contents and fluorosurfactant contents in amounts of 0.0001, 0.001, and 0.01 weight percent provided superior combing characteristics to comparable hair conditioning compositions without a fluorosurfactant component and to hair conditioning compositions with fluorosurfactant contents in amounts of 0.1 weight percent and above. Although the reasons for the enhanced conditioning effectiveness of the conditioning compositions of this invention are not fully understood, and without intending to be bound by the same, it is believed that an interdependency exists between the fluorosurfactant and the fatty alcohol(s) components of the composition.

The essential components of formulations according to the present invention, as indicated above, are (1) a cationic hair conditioning agent, (2) a non-ionic surfactant, (3) a fatty alcohol, (4) a fluorosurfactant, and (5) a water phase.

Cationic Hair Conditioning Agent

Cationic hair conditioning agents used in the present formulations are quaternary ammonium salts, fatty amines and salts thereof well known to those skilled in the art. Suitable quaternary ammonium salts may be of the formula

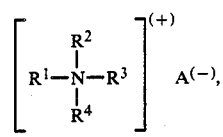

where $R^1$ is an alkyl group having 8–30 carbons; $R^2$ is an alkyl group having 1–30 carbons, an aryl group of 6–13 carbons, or $-(CH_2-CH_2-O)_xCH_2-CH_2OH$, where x is an integer between 0 and 20, inclusive; $R^3$ and $R^4$ are, independently, an alkyl group having 1–4 carbons, or $-(CH_2-CH_2-O)_xCH_2-CH_2OH$, where x is an integer between 0 and 10, inclusive; and A is a halogen, $CH_3OSO_3$, or $H_2PO_4$.

Suitable quaternary ammonium salts also include pyridinium salts having the structure

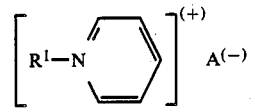

and

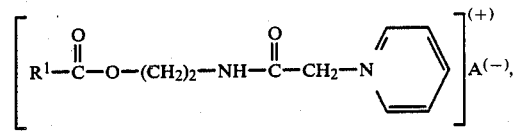

where $R^1$ is an alkyl group having 8–30 carbons and A is a halogen.

Other examples of suitable quaternary ammonium salts have the structure

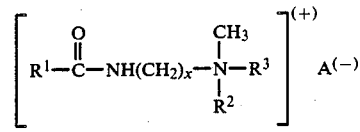

and

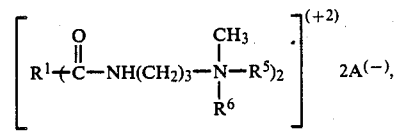

where $R^1$ is an alkyl group having 8–30 carbons; $R^2$ is either a lower alkyl group (1–4 carbons) or $-(CH_2CH_2-O)_yCH_2-CH_2OH$, where y is an integer between 0 and 10, inclusive; $R^3$ is $-(CH_2-CH_2-O)_yCH_2-CH_2OH$, where y is an integer between 0 and 10, inclusive,

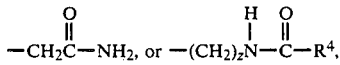

where z is either 2 or 3, and $R^4$ is an alkyl group having 8-30 carbons; x is 2 or 3; $R^5$ is a lower alkyl group (1-4 carbons); $R^6$ is a lower alkyl group (1-4 carbons), an aryl group having 6-13 carbons, or

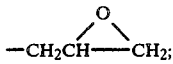

and A is halogen, $C_2H_5OSO_3$, or $CH_3OSO_3$.

A Preferred group of conditioning agents include quaternary ammonium compounds identified by the names Quaternium-18, cetrimonium chloride, steralkonium chloride, lauralkonium chloride and dicetyldimonium chloride as identified in the CTFA Cosmetic Ingredient Dictionary, Third Edition, 1982, published by the Cosmetic Toiletry and Fragrance Association, Inc., hereinafter referred to as the CTFA Dictionary, and which Dictionary names other compositions mentioned hereinafter. Formulations of the invention preferably contain the cationic hair conditioning ingredient(s) at a concentration of 0.2-5 weight percent as an active ingredient.

Non-ionic Surfactant

Non-ionic surfactants used in the present formulations include ethers having the formula $R^1-O(C_2H_4O)_xH$, where $R^1$ is an alkyl group having 8-30 carbons, and x is an integer between 2 and 100, inclusive. These ethers are per se known in the art. Other non-ionic surfactants include esters having the structure $$(R^1-\overset{O}{\underset{\|}{C}}-O)_x-R^2,$$

where x is an an integer between 1 and 3, inclusive; $R^1$ is an alkyl group having 8-30 carbons; and $R^2$ is $(C_2H_4O)_yH$, where y is an integer between 2 and 100, inclusive, or a sugar moiety, such as sorbitol, sucrose, or methyl glucose. These esters are per se known in the art.

Formulations of the invention preferably contain the non-ionic surfactant ingredient at a concentration of 0.1-5%, more preferably 0.25-5% as an active ingredient.

Fatty Alcohol

Fatty alcohols used in the present formulations are primary or secondary alcohols having 8-32 carbons. They include straight-chained, branched, saturated, and unsaturated structures and can be used alone or in admixture with each other. The preferred fatty alcohols are straight-chained, primary alcohols having 10-26 carbons, including without limitation, lauryl, tridecyl, myristyl, cetyl, stearyl, oleyl, behenyl, arachyl, carnaubyl, and ceryl alcohols. In addition, mixtures of natural or synthetic fatty alcohols having fatty chain links of from 8-32 carbons are also useful. Several such mixtures are commercially available.

The fatty alcohol, or mixture of fatty alcohols, is preferably present in formulations of the invention in a concentration of 0.5-10 weight percent and, more preferably, 2-5 weight percent as an active ingredient.

Fluorosurfactant

Fluorosurfactants used in the present formulations are hydrophobic-lipophobic perfluorinated compounds which can be represented by the formula $$(C_nF_{2n+1})-R-Q$$

wherein n is an integer from 4 to 18, R is selected from the group consisting of $-X-$, $-Y-O-Z-$, $-Y-S-Z-$,

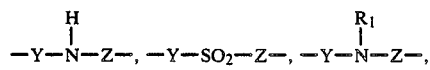

$-Y-CONH-Z-$, $-Y-SO_2NH-Z-$, wherein X is $(CH_2)_x$, Y is $(CH_2)_y$ and Z is $(CH_2)_z$, $R_1$ is an alkyl group containing from 1 to 4 carbon atoms, wherein x is an integer from 1 to 6, the terminal $(CH_2)_y$ group is attached to the $(C_nF_{2n+1})$ portion of the molecule, the terminal $(CH_2)_z$ group is attached to the Q portion of the molecule Y is an integer from 0 to 3, z is an integer from 1 to 3, and Q is selected from the group of $-O(CH_2CH_{O2})_xH$, where $x=1-10$;

$-CO_2M$, where M is an alkali metal (e.g. Na, K, Li);

$-{}^{30}N(CH_3)_3CH_3SO_4{}^-$.

Commercially available surfactants which fall within the definition of this formula include Zonyl FSA, an anionic fluorochemical surfactant ($R_fCH_2CH_2SCH_2CH_2CO_2Li$) manufactured by E. I. DuPont de Nemours & Company; Zonyl FSC, a cationic fluorochemical surfactant ($R_fCH_2CH_2SCH_2CH_2N(CH_3)_3CH_3SO_4$) manufactured by E. I. DuPont de Nemours & Company; Zonyl FSN, a nonionic fluorochemical surfactant ($R_fCH_2CH_2O(CH_2CH_2O)_xH$) manufactured by E. I. DuPont de Nemours & Company; Lodyne S-106B—a cationic fluorochemical surfactant of the fluoroalkyl ammonium chloride type manufactured by Ciba-Geigy; and Lodyne S-112B—a blend of an anionic fluorochemical sodium sulfonate type and a nonionic fluorochemical synergist of the fluoroalkyl amide type manufactured by Ciba-Geigy. Formulations of the invention contain a small but effective amount of fluorosurfactant, preferably present at from 0.00001-0.01 percent, and more preferably, from 0.0001-0.001 weight percent of the composition as an active ingredient.

Optional Components

The conditioning composition may include a fatty amine. The fatty amines are secondary cationic surfactants that enhance the activity of the conditioner, although the conditioner is effective without such an ingredient. Examples of fatty amines are of the structure

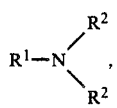

where $R^1$ is an alkyl group of 8-30 carbons and $R^2$ is a lower alkyl group (1-4 carbons); $R^1$ is a lower alkyl group (1-4 carbons) and $R^2$ is an alkyl group of 8-30 carbons; $R^1$ is $—(C_2H_4O)_xH$, where x is an integer of between 1 and 50, inclusive, and $R^2$ is

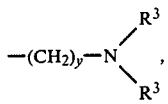

where y is 2 or 3 and $R^3$ is $—(C_2H_4O)_zH$, where z is an integer between 1 and 15, inclusive.

Other fatty amines that can be used as an optional component in the formulations are of the structure

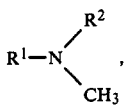

where $R^1$ is an alkyl group having 8-30 carbons, and $R^2$ is $—(C_2H_4O)_xH$, where x is an integer between 1 and 50, inclusive; and those having the structure

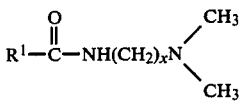

where $R^1$ is an alkyl group having 8-30 carbons, and x is either 2 or 3.

Where it is desired to use a fatty amine as a component of a formulation, the preferred concentration of the fatty amine, or mixture thereof, is 0.1-3 weight percent.

Ingredients in addition to water and the previously discussed ingredients can also be present in compositions of this invention. These ingredients include, but are not limited to components such as viscosity builders (e.g., NaCl or KCl), perfumes, buffers (e.g., citric acid), and preservatives.

Water Phase

The water phase makes up the remainder of the conditioning composition. Deionized water is preferred.

Hair conditioner compositions of the invention suitably are near neutral to slightly acidic in pH value, and preferably have pH values of from about 4 to about 7, and more preferably from about 4.5 to about 5.5.

Methods of Manufacture

Many methods of combining the ingredients of the hair conditioning compositions of the present invention are available. In an illustrative process, the water, cationic hair conditioning agent, buffer (optional), and fatty amine (optional) are combined and heated to about 63° C. The fatty alcohol(s) and non-ionic surfactant are added with moderate agitation, and the mixture heated to 72° C., where the temperature is maintained for 30 minutes. The mixture is allowed to cool. At 60° C., optional ingredients such as a preservative are added and, at 45° C., the fluorosurfactant and other optional ingredients such as a fragrance are added.

Use

Hair conditioning compositions of the present invention are preferably used on freshly-shampooed hair. From about one gram to about sixty grams of the composition, preferably from about five grams to about thirty grams, are applied to the hair, gently worked or combed through to be evenly distributed, and then rinsed from the hair. Alternatively, the composition may be left on the freshly-shampooed hair, or may be applied to dry hair between shampooings to aid in combing and manageability.

The following examples illustrate hair conditioning compositions. Unless otherwise indicated, all percentages herein are by weight of the active ingredient.

The following composition was prepared by the general method as set forth above.

EXAMPLE 1

| Ingredient | Concentration |
| --- | --- |
| Cetyl alcohol | 3.0 |
| Stearyl alcohol | 0.8 |
| Fluorosurfactant DuPont Zonyl FSC | 0.0005 |
| Dicetyldimonium chloride | 2.25 |
| Ceteareth-20 | 0.3 |
| Stearamidopropyl dimethylamine | 0.5 |
| Potassium chloride | 0.3 |
| Citric Acid | 0.09 |
| DL Panthenol | 0.1 |
| Fragrance | 0.3 |
| Preservative Methylchloroisothiazolinone and methylisothiazolinone (Kathon CG (Rohm & Haas)) | 0.0006 |
| Deionized water | to 100 |

Hair was treated with such a composition following usual conditioning product evaluation methods. The composition provided wet hair with good combing characteristics. Monadic testing under natural use conditions of this composition as compared with commercially available state-of-the-art fluorosurfactant-free hair conditioning compositions that contained fatty alcohols and that contained volatile silicones indicated superior wet and dry combing, detangling, texture, manageability, cleaning, oiliness, fly-away hair, sticky/gummy, and product consistency characteristics of the composition of Example 1.

Variations of Example 1

Formulations were prepared in which the components listed in Example 1 remained constant except for the fluorosurfactant; Zonyl FSA, Zonyl FSN, Lodyne 106B, and Lodyne 112B were substituted for Zonyl FSC; and formulations were prepared in which water was substituted for the fluorosurfactant and in which the concentration of the selected fluorosurfactant (including Zonyl FSC) was changed to the following: 0.0001%, 0.001%, and 0.01%. "Permed" hair (hair that has been subjected to permanent waving (thioglycolate and subsequent neutralization) was treated with each of these compositions and compared with the composition of Example 1 in accordance with conventional testing procedures. These comparisions indicated combing properties resulting from the use of the fluorosurfactant-containing formulations were superior to combing properties resulting from the use of the fluorosurfactant-free formulations, while combing properties resulting from the use of the formulations containing 0.0005% fluorosurfactant were superior to combing properties of the other fluorosurfactant containing formulations of this Example.

EXAMPLE 2

| Ingredient | Concentration |
| --- | --- |
| Cetyl alcohol | 3.3 |
| Stearyl alcohol | 0.8 |
| Behenyl alcohol | 0.3 |
| Fluorosurfactant Zonyl FSC | 0.0005 |
| Dicetyldimonium chloride | 2.25 |
| Ceteareth-20 | 0.3 |
| Stearamidopropyl dimethylamine | 0.5 |
| Potassium chloride | 0.2 |
| Citric Acid | 0.09 |
| DL Panthenol | 0.15 |
| Fragrance | 0.3 |
| Preservative | 0.0006 |
| Deionized water | to 100 |

"Permed" hair was treated with the composition of Example 2 and the resulting evaluation indicated superior combing properties resulting from the use of this fluorosurfactant containing formulation.

EXAMPLE 3

| Ingredient | Concentration |
| --- | --- |
| Cetyl alcohol | 1.7 |
| Stearyl alcohol and Ceteareth-20 (Amerchol Promulgen G) | 1.0 |
| Fluorosurfactant DuPont Zonyl FSC | 0.0005 |
| Dicetyldimonium chloride | 1.70 |
| Stearamidopropyl dimethylamine | 0.3 |
| Hydroxyethylcellulose Natrosol 250 HHR (2%) | 0.7 |
| DL Panthenol | 0.2 |
| Methyl paraben | 0.2 |
| Propyl paraben | 0.2 |
| Citric acid | 0.1 |
| Sodium hydroxide | 0.02 |
| Deionized water | q.s. to 100 |

Variations of Example 3

Formulations were prepared in which the components listed in Example 3 remained constant except for the fluorosurfactant; Zonyl FSA, Zonyl FSN, Lodyne 106B, and Lodyne 112B were substituted for Zonyl FSC; and formulations were prepared in which water was substituted for the fluorosurfactant (similatilng a commercially available hair conditioner), and in which the concentration of the selected fluorosurfactant (including Zonyl FSC) was changed to the following amounts: 0.0001%, 0.001%, and 0.01%. "Permed" hair was treated with each of these compositions and compared with the composition of Example 1 in accordance with conventional testing procedures. These comparisons indicated combing properties resulting from the use of the fluorosurfactant containing formulations were superior to combing properties resulting from the use of the fluorosurfactant-free formulations, while combing properties resulting from the use of the formulations containing 0.0005% fluorosurfactant were superior to combing properties of the other fluorosurfactant containing formulations of this Example.

EXAMPLE 4

| Ingredient | Concentration |
| --- | --- |
| Cetyl alcohol | 3.0 |
| Quaternium-18 | 1.5 |
| Fluorosurfactant Zonyl FSC | 0.0005 |
| PEG-150 Distearate | 2.5 |
| Dimethyl stearamine | 0.5 |
| Citric acid | 0.1 |
| Deionized water | q.s. to 100 |

"Permed" hair was treated with the composition of Example 4 and with the composition of this Example in which water was substituted for the fluorosurfactant. The resulting evaluation indicated superior combing properties resulted from the use of the fluorosurfactant containing formulation.

EXAMPLE 5

| Ingredient | Concentration |
| --- | --- |
| Cetyl alcohol | 3.0 |
| Fluorosurfactant DuPont Zonyl FSC | 0.0005 |
| Stearalkonium chloride | 1.4 |
| Steareth-2 | 1.5 |
| Dimethyl stearamine | 0.5 |
| Citric acid | 0.1 |
| Deionized water | q.s. to 100 |

"Permed" hair was treated with the composition of Example 5 and with the composition of this Example in which water was substituted for the fluorosurfactant. The resulting evaluation indicated superior combing properties resulted from the use of the fluorosurfactant containing formulation.

EXAMPLE 6

| Ingredient | Concentration |
| --- | --- |
| Cetyl alcohol | 3.0 |
| Fluorosurfactant DuPont Zonyl FSC | 0.0005 |
| Cetrimonium chloride | 1.75 |
| Ceteth-2 | 2.0 |
| Dimethyl stearamine | 0.75 |
| Citric acid | 0.1 |
| Deionized water | q.s. to 100 |

"Permed" hair was treated with the composition of Example 6 and with the composition of this Example in which water was substituted for the fluorosurfactant. The resulting evaluation indicated superior combing properties resulted from the use of the fluorosurfactant containing formulation.

EXAMPLE 7

| Ingredient | Concentration |
| --- | --- |
| Cetyl alcohol | 8.0 |
| Stearyl alcohol | 0.8 |
| Fluorosurfactant DuPont Zonyl FSC | 0.0005 |
| Dicetyldimonium chloride | 2.25 |
| Ceteareth-20 | 0.5 |
| Stearamidopropyl dimethylamine | 0.5 |
| Potassium chloride | 0.2 |

| Ingredient | Concentration |
| --- | --- |
| Citric Acid | 0.1 |
| DL Panthenol | 0.1 |
| Preservative | 0.0005 |
| Deionized water | to 100 |

"Permed" hair was treated with the composition of Examples 1 and 7 and with the composition of this Example in which water was substituted for the fluorosurfactant. The resulting evaluation indicated superior combing properties resulted from the use of the fluorosurfactant containing formulations, while the combing properties of the formulation of Example 1 were superior to the combing properties of the formulation of this Example.

EXAMPLE 8

| Ingredient | Concentration |
| --- | --- |
| Cetyl alcohol | 3.0 |
| Fluorosurfactant DuPont Zonyl FSC | 0.0005 |
| Dicetyldimonium chloride | 2.25 |
| Steareth-21 | 1.5 |
| Deionized water | q.s. to 100 |

"Permed" hair was treated with the composition of Example 8 and with the composition of this Example in which water was substituted for the fluorosurfactant. The resulting evaluation indicated superior combing properties resulted from the use of the flourosurfactant containing formulation.

EXAMPLE 9

| Ingredient | Concentration |
| --- | --- |
| Glyceryl monostearate | 3.0 |
| Fluorosurfactant DuPont Zonyl FSC | 0.0005 |
| Dicetyldimonium chloride | 2.25 |
| Steareth-21 | 1.5 |
| Deionized water | q.s. to 100 |

"Permed" hair was treated with the compositions of Examples 8 and 9 and with the composition of this Example in which water was substituted for the fluorosurfactant. The resulting evaluation indicated superior combing properties resulted from the use of the fluorosurfactant containing formulation of Example 8 and that the combing properties resulting from the use of the formulations of this Example (both fluorosurfactant-containing and fluorosurfactant-free) were inferior to the combing properties resulting from the use of the fluorosurfactant containing formulation of Example 8.

EXAMPLE 10

| Ingredient | Concentration |
| --- | --- |
| Stearyl alcohol | 0.3 |
| Fluorosurfactant DuPont Zonyl FSC | 0.0005 |
| Glyceryl monostearate | 0.44 |
| Stearalkonium chloride | 1.14 |
| Ceteth-2 | 0.75 |
| Dimethyl stearamine | 0.67 |
| Citric acid | 1.6 |
| Phenoxyethanol | 0.5 |
| Sodium chloride | 0.4 |
| Sodium hydroxide | 0.133 |
| Deionized water | q.s. to 100 |

VARIATIONS OF EXAMPLE 10

Formulations were prepared in which the components listed in Example 10 remained constant except for the fluorosurfactant; Zonyl FSA, Zonyl FSN, Lodyne 106B, and Lodyne 112B were substituted for Zonyl FSC; and formulations were prepared in which water was substituted for the fluorosurfactant and in which the concentration of the selected fluorosurfactant (including Zonyl FSC) was changed to the following amounts: 0.0001%, 0.001%, and 0.01%. "Permed" hair was treated with each of these compositions and compared with the composition of Examples 1 and 10 in accordance with conventional testing procedures. These comparisions indicated combing properties resulting from the use of the fluorosurfactant containing formulations of Example 10 and its variations were inferior to combing properties resulting from the use of the fluorosurfactant-free formulations, while combing properties resulting from the use of the Example 1 formulation was superior to combing properties of the fluorosurfactant-free formulation of this Example.

EXAMPLE 11

| Ingredient | Concentration |
| --- | --- |
| Cetyl alcohol | 3.0 |
| Stearyl alcohol | 0.8 |
| Fluorosurfactant DuPont Zonyl FSC | 0.0005 |
| Ceteareth-20 | 0.5 |
| Stearamidopropyl dimethylamine | 1.25 |
| Potassium chloride | 0.2 |
| Citric Acid | 0.1 |
| DL Panthenol | 0.1 |
| Preservative | 0.0006 |
| Deionized water | to 100 |

"Permed" hair was treated with the composition of Examples 1 and 11 and with the composition of this Example in which water was substituted for the fluorosurfactant. The resulting evaluation indicated superior combing properties resulted from the use of the fluorosurfactant containing formulations, while the combing properties of the formulation of Example 1 were superior to the combing properties of the fluorosurfactant containing formulation of this Example.

While particular embodiments of the invention have been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. A hair conditioning composition comprising a cationic hair conditioning agent, a fatty alcohol, a fluorosurfactant, said fluorosurfactant being present in proportions, based on the weight of the composition, less than about 0.01 percent, a nonionic surfactant, and water.

2. The composition of claim 1 wherein said composition comprises from about 0.2 percent to about five percent of said cationic conditioning agent, from 0.00001–0.01 weight percent of said fluorosurfactant, and from about 0.5 percent to about ten percent of said fatty alcohol component.

3. The composition of claim 2 wherein said cationic hair conditioning agent is selected from the group consisting of quaternary ammonium salts, fatty amines and salts thereof.

4. The composition of claim 1 wherein said fluorosurfactant has the general formula

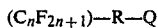
$$(C_nF_{2n+1})-R-Q$$

wherein n is an integer from 4 to 18, R is selected from the group consisting of —X—, —Y—O—Z—, —Y—S—Z—,

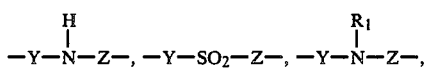
$$-Y-\overset{\overset{H}{|}}{N}-Z-, -Y-SO_2-Z-, -Y-\overset{\overset{R_1}{|}}{N}-Z-,$$

—Y—CONH—Z—, —Y—SO$_2$NH—Z—, wherein X is (CH$_2$)$_x$, Y is (CH$_2$)$_y$ and Z is (CH$_2$)$_z$, R$_1$ is an alkyl group containing from 1 to 4 carbon atoms, wherein x is an integer from 1 to 6, the terminal (CH$_2$)$_y$ group is attached to the (C$_n$F$_{2n+1}$) portion of the molecule, the terminal (CH$_2$)$_z$ group is attached to the Q portion of the molecule Y is an integer from 0 to 3, z is an integer from 1 to 3, and Q is selected from the group of
—O(CH$_2$CH$_2$O)$_x$H, where x=1–10;
—CO$_2$M, where M is an alkali metal;
—$^+$N(CH$_3$)$_3$CH$_3$SO$_4$$^-$.

5. The composition of claim 1 wherein said composition contains from about 0.1 to about five percent of said nonionic surfactant.

6. The composition of claim 1 wherein said composition contains from about 0.5 to about ten percent of said fatty alcohol component.

7. The composition of claim 1 wherein said fatty alcohol component is a straight-chained, primary alcohol selected from the group consisting of lauryl, tridecyl, myristyl, cetyl, stearyl, oleyl, behenyl, arachyl, carnaubyl, and ceryl alcohols.

8. The composition of claim 1 wherein said cationic conditioning agent is selected from the group consisting of Quaternium-18, cetrimonium chloride, stearalkonium chloride, lauralkonium chloride and dicetyldimonium chloride.

9. The composition of claim 8 wherein said composition contains from about 0.2 to about five percent of said cationic conditioning agent.

10. The composition of claim 1 wherein said fluorosurfactant is selected from the group consisting of cationic, anionic, and nonionic fluorosurfactants.

11. The composition of claim 1 wherein its pH value is in the range of about 4 to about 7.

12. The composition of claim 11 wherein said composition comprises from about 0.2 percent to about five percent of said cationic conditioning agent, and said cationic hair conditioning agent is selected from the group consisting of quaternary ammonium salts, fatty amines and salts thereof; from 0.0001–0.001 weight percent of said fluorosurfactant, and said fluorosurfactant is selected from the group consisting of cationic, anionic, and nonionic fluorosurfactants; and from about 0.5 to about ten percent of said fatty alcohol component, and said fatty alcohol component is a straight-chained, primary alcohol selected from the group consisting of lauryl, tridecyl, myristyl, cetyl, stearyl, oleyl, behenyl, arachyl, carnaubyl, and ceryl alcohols.

13. A hair conditioning composition in the form of a stable oil-in-water emulsion that contains a cationic hair conditioning agent, a fatty alcohol, a fluorosurfactant, a nonionic surfactant, and water, the amount of said fluorosurfactant in said composition being 0.00001–0.01 percent by weight, and the amount of said fatty alcohol in said composition being in the range of about 0.5–ten percent by weight.

14. A hair conditioning composition in the form of a stable oil-in-water emulsion that contains a cationic hair conditioning agent, a fatty alcohol, a fluorosurfactant, a nonionic surfactant, and water, the amount of said fluorosurfactant in said composition being 0.00001–0.01 percent by weight, and the amount of said fatty alcohol in said composition being in the range of about 0.5–ten percent by weight.

15. The composition of claim 14 wherein said fluorosurfactant is selected from the group consisting of cationic, anionic, and nonionic fluorosurfactants.

16. The composition of claim 15 wherein said fluorosurfactant has the general formula

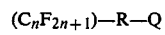
$$(C_nF_{2n+1})-R-Q$$

wherein n is an integer from 4 to 18, R is selected from the group consisting of —X—, —Y—O—Z—,—Y—S—Z—,

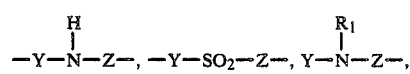
$$-Y-\overset{\overset{H}{|}}{N}-Z-, -Y-SO_2-Z-, Y-\overset{\overset{R_1}{|}}{N}-Z-,$$

—Y—CONH—Z— Y—SO$_2$NH—Z—, wherein X is (CH$_2$)$_x$, Y is (CH$_2$)$_y$ and Z is (CH$_2$)$_z$, R$_1$ is an alkyl group containing from 1 to 4 carbon atoms, wherein x is an integer from 1 to 6, the terminal (CH$_2$)$_y$ group is attached to the (C$_n$F$_{2n+1}$) portion of the molecule, the terminal (CH$_2$)$_z$ group is attached to the Q portion of the molecule, y is an integer from 0 to 3, z is an integer from 1 to 3, and Q is selected from the group of
—O(CH$_2$CH$_2$O)$_x$H, where x=1–10;
—CO$_2$M, where M is an alkali metal (e.g. Na, K, Li);
—$^+$N(CH$_3$)$_3$CH$_3$SO$_4$$^-$.

17. The composition of claim 15 wherein the amount of said fluorosurfactant in said composition is about 0.0005 percent by weight.

18. The composition of claim 15 wherein said composition contains from about two to about five percent of said fatty alcohol component.

19. The composition of claim 18 wherein said fatty alcohol component is a straight-chained, primary alcohol selected from the group consisting of lauryl, tridecyl, myristyl, cetyl, stearyl, oleyl, behenyl, arachyl, carnaubyl, and ceryl alcohols.

20. The composition of claim 18 wherein said composition comprises from about 0.2 percent to about five percent of said cationic conditioning agent, and said cationic hair conditioning agent is selected from the group consisting of quaternary ammonium salts, fatty amines and salts thereof.

21. The composition of claim 20 wherein said composition contains from about 0.1 to about five percent of said nonionic surfactant.

22. The composition of claim 21 wherein said composition further includes from about 0.1 to about three weight percent of a fatty amine.

23. The composition of claim 21 wherein said composition has a pH value of from about 4.5 to about 5.5.

24. The composition of claim 23 wherein the amount of said fluorosurfactant in said composition is about 0.0005 percent by weight, said fluorosurfactant has the general formula $$(C_nF_{2n+1})-R-Q$$

wherein n is an integer from 4 to 18, R is selected from the group consisting of —X—, —Y—O—Z—, —Y—S—Z—, $$-Y-\underset{H}{N}-Z-, \quad -Y-SO_2-Z-, \quad -Y-\underset{R_1}{N}-Z-,$$

—Y—CONH—Z—, —Y—SO$_2$NH—Z—, wherein X is $(CH_2)_x$, Y is $(CH_2)_y$ and Z is $(CH_2)_z$, $R_1$ is an alkyl group containing from 1 to 4 carbon atoms, wherein x is an integer from 1 to 6, the terminal $(CH_2)_y$ group is attached to the $(C_nF_{2n+1})$ portion of the molecule, the terminal $(CH_2)_z$ group is attached to the Q portion of the molecule Y is an integer from 0 to 3, z is an integer from 1 to 3, and Q is selected from the group consisting of —O(CH$_2$CH$_2$O)$_x$H, where x=1-10;

—CO$_2$M, where M is an alkali metal and

—$^+$N(CH$_3$)$_3$CH$_3$SO$_4^-$.

said composition further includes from about 0.1 to about three weight percent of a fatty amine.

25. The composition of claim 14 wherein said composition comprises from about 0.2 percent to about five percent of said cationic conditioning agent, and said cationic hair conditioning agent is selected from the group consisting of quaternary ammonium salts, fatty amines and salts thereof; from 0.0001-0.001 weight percent of said fluorosurfactant, and said fluorosurfactant is selected from the group consisting of cationic, anionic, and nonionic fluorosurfactants; and from about 0.5 to about ten percent of said fatty alcohol component, and said fatty alcohol component is a straight-chained, primary alcohol selected from the group of lauryl, tridecyl, myristyl, cetyl, stearyl, oleyl, behenyl, arachyl, carnaubyl, and ceryl alcohols.

* * * * *